United States Patent [19]

Andrew et al.

[11] 4,051,175
[45] Sept. 27, 1977

[54] PHOSPHONOPHENYLAMINONAPHTHALENE COMPOUNDS

[75] Inventors: Herbert Francis Andrew; Cecil Vivian Stead; Ronald Thompson, all of Manchester, England

[73] Assignee: Imperial Chemical Industries Limited, London, England

[21] Appl. No.: 682,047

[22] Filed: Apr. 30, 1976

[30] Foreign Application Priority Data

May 16, 1975   United Kingdom ............. 20848/75

[51] Int. Cl.² .................... C07F 9/38; C09B 29/00
[52] U.S. Cl. .......................... 260/502.5; 260/196
[58] Field of Search ...................... 260/502.5

[56] References Cited

U.S. PATENT DOCUMENTS

| | | | |
|---|---|---|---|
| 2,227,963 | 1/1941 | Dickey et al. | 260/502.5 |
| 2,328,358 | 8/1943 | Pike | 260/502.5 |
| 2,381,071 | 8/1945 | McNally et al. | 260/502.5 |
| 3,288,846 | 11/1966 | Irani et al. | 260/502.5 |

Primary Examiner—Joseph E. Evans
Attorney, Agent, or Firm—Cushman, Darby & Cushman

[57] ABSTRACT

Naphthalene compounds of the formula:

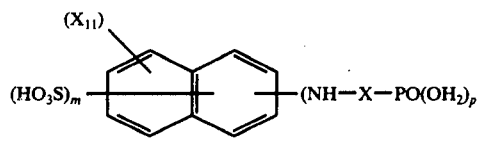

wherein
 $m$ is 0, 1 or 2
 $n$ is 0 or can be 1 if $m$ is 1 or 2, in which case $X_1$ is $NH_2$ or OH in $m$ position to a $SO_3H$ group
 X is a divalent alkylene, aralkylene or arylene radical, which may be substituted and
 $p$ is 1 or 2.

The new compounds are useful dyestuff intermediates, especially as coupling components for the manufacture of azo dyestuffs.

5 Claims, No Drawings

PHOSPHONOPHENYLAMINONAPHTHALENE COMPOUNDS

This invention relates to new naphthalene compounds and more particularly to new naphthalene compounds valuable for use in the synthesis of dyestuffs.

According to the invention, there are provided compounds of the formula:

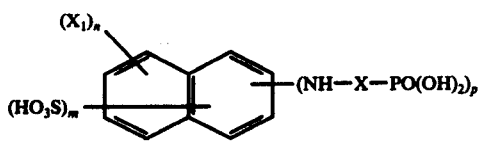

(1)

wherein
- $m$ is 0, 1 or 2
- $n$ is 0 or can be 1 if $m$ is 1 or 2, in which case $X_1$ is $NH_2$ or OH in $m$ position to a $SO_3H$ group
- X is a divalent alkylene, aralkylene or arylene radical, which may be substituted, and
- $p$ is 1 or 2.

An alkylene group represented by X in formula (1) may be straight chain or branched, and may contain OH. It preferably contains less than 6 carbon atoms, e.g. methylene, trimethylene, tetramethylene, propylene, hexamethylene or hydroxypropylene, but the preferred alkylene radical is ethylene.

An aralkylene radical represented by X is preferably m- or p-benzylene, having the NH group preferably attached to the benzene nucleus and the phosphorus atom preferably attached to the methylene group. An arylene radical represented by X is preferably a phenylene or naphthylene radical, and in the first case is preferably m- or p-phenylene, optionally substituted by $CH_3$, F, Cl, Br or $NO_2$; in the case of naphthylene is preferably a 1,3-, 1,6-, 1,7- or 2,7-naphthylene radical, optionally substituted by $SO_3H$.

The invention also provides a process for manufacture of the new naphthalene compounds which comprises heating together a naphthalene compound of the formula:

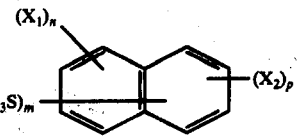

(2)

wherein $X_1$, $m$, $n$ and $p$ have the meanings stated above and $X_2$ is OH, $NH_2$ or NHR, where R is an alkyl group of 1 to 4 carbon atoms, which is not in meta position to $SO_3H$, and an amine of the formula:

$$NH_2 - X - PO(OH)_2 \qquad (3)$$

wherein X has the meaning stated above, in the presence of an aqueous solution of an alkali metal bisulphite.

The process can be carried out under a variety of conditions according to the ease with which the group $X_2$ is replaced by the group $NH - X - PO(OH)_2$. As a general rule, compounds in which $X_2$ is $NH_2$ react more readily than the corresponding OH or NHR compound; also the presence of $SO_3H$ in ortho position to $X_2$ lowers the reactivity of the latter so that higher reaction temperatures are desirable. As a general rule also, the compounds of formula (3) in which X is alkylene or aralkylene are more reactive than those in which X is arylene. Within these broad limitations it is sometimes possible to effect the reaction at from 90° C upwards, but it is usually more practical to operate within the range of 100°–200° C in order to achieve a satisfactory rate of reaction.

It is usually preferable to use a small excess of the compound of formula (3) over the theoretical amount required for reaction. The new compounds can be isolated by acidification and boiling to decompose sulphites followed by filtration. In some cases salting or spray drying may be necessary.

The following table gives examples of naphthalene compounds which can be used in the above process, together with an indication of the kinds of product obtained therefrom; as can be seen from the table, there is frequently a choice of starting material for preparing a class of the new naphthalene compounds.

| Starting material | | |
|---|---|---|
| 1-naphthol<br>1-naphthylamine | 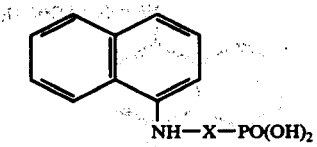 | (4) |
| 2-naphthol<br>2-naphthylamine | 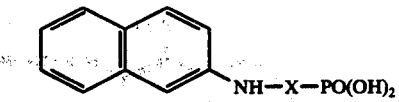 | (5) |
| 1,2-dihydroxynaphthalene<br>1-amino-2-naphthol | 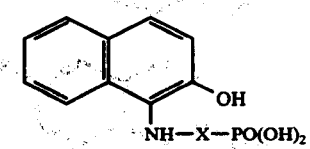 | (6) |

-continued

| Starting material | | |
|---|---|---|
| 1,4-dihydroxynaphthalene<br>1-amino-4-naphthol | 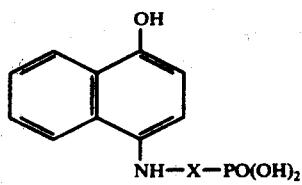 | (7) |
| | and 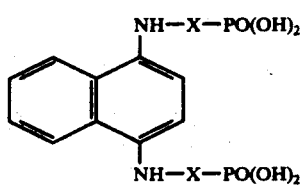 | (8) |
| 1,5-dihydroxynaphthalene<br>1-amino-5-hydroxynaphthalene | 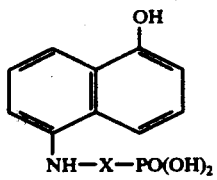 | (9) |
| | and 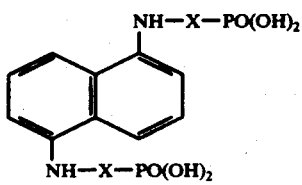 | (10) |
| 1-amino-8-naphthol | 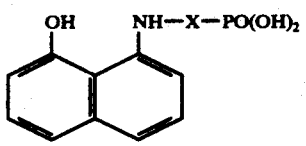 | (11) |
| 2,7-dihydroxynaphthalene | 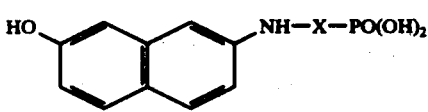 | (12) |
| | and 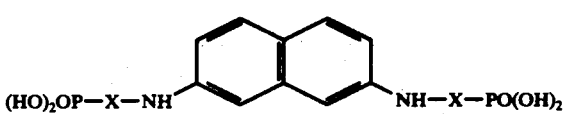 | (13) |
| 1-naphthol-4-sulphonic acid<br>1-aminonaphthalene-4-sulphonic acid<br>1-methylaminonaphthalene-4-sulphonic acid | 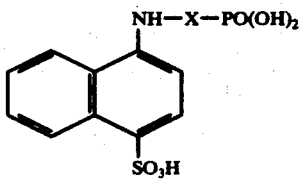 | (14) |
| 2-naphthol-1-sulphonic acid<br>Tobias acid<br>N-methyl Tobias acid | 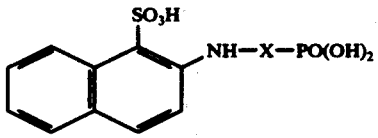 | (15) |
| 2-naphthol-6-sulphonic acid<br>2-aminonaphthalene-6-sulphonic acid<br>2-methylaminonaphthalene-6-sulphonic acid | 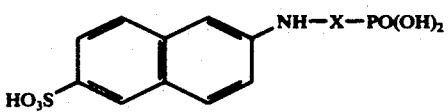 | (16) |

-continued

| Starting material | | |
|---|---|---|
| 2-naphthol-7-sulphonic acid 2-aminonaphthalene-7-sulphonic acid | 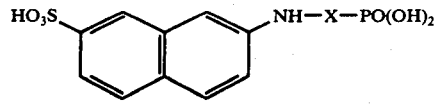 | (17) |
| 2-naphthol-8-sulphonic acid 2-aminonaphthalene-8-sulphonic acid | 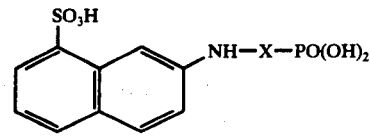 | (18) |
| 2-naphthol-5,7-disulphonic acid | 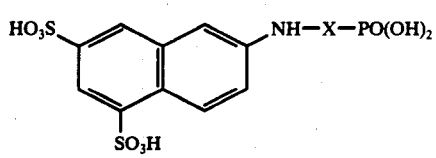 | (19) |
| 2-naphthol-6,8-disulphonic acid 2-aminonaphthalene-6,8-disulphonic acid | 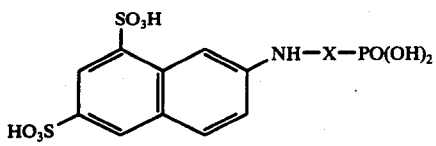 | (20) |
| 1-aminonaphthalene-6-sulphonic acid | 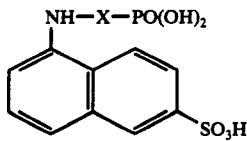 | (21) |
| 1-aminonaphthalene-7-sulphonic acid | 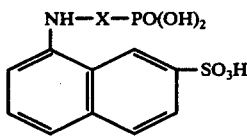 | (22) |
| 1,5-dihydroxynaphthalene-4-sulphonic acid 1-amino-5-naphthol-4-sulphonic acid | 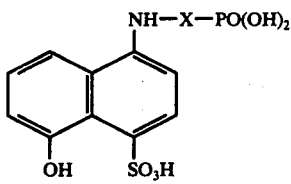 | (23) |
| | and 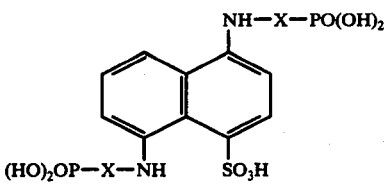 | (24) |
| 1,5-diaminonaphthalene-4-sulphonic acid | Formula (24) | |
| 1,5-dihydroxynaphthalene-7-sulphonic acid 1-amino-5-naphthol-7-sulphonic acid | 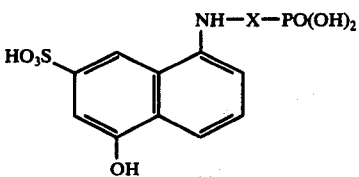 | (25) |
| 1-amino-5-naphthol-2-sulphonic acid | 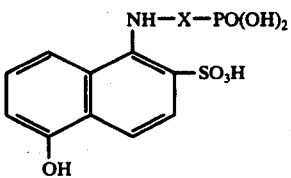 | (26) |

| Starting material | | |
|---|---|---|
| | and 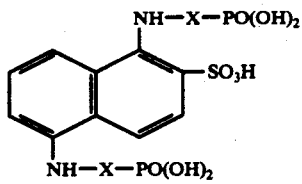 | (27) |
| 1,7-dihydroxynaphthalene-4-sulphonic acid<br><br>1-amino-7-naphthol-4-sulphonic acid<br><br>1-methylamino-7-naphthol-4-sulphonic acid | 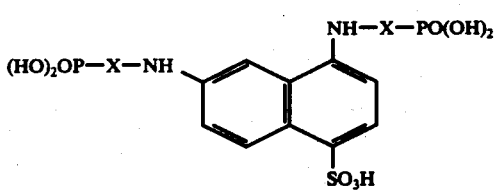 | (28) |
| | and 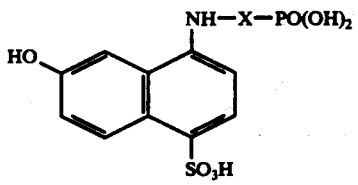 | (29) |
| 1-amino-5-naphthol-8-sulphonic acid | 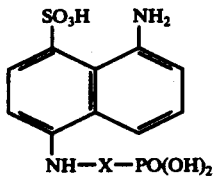 | (30) |
| 2,5-dihydroxynaphthalene-7-sulphonic acid<br><br>2-amino-5-naphthol-7-sulphonic acid<br><br>2-methylamino-5-naphthol-7-sulphonic acid | 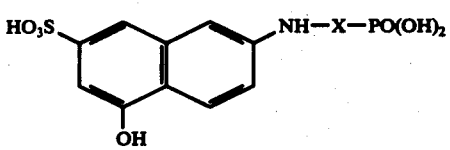 | (31) |
| 2-amino-5-naphthol-1-sulphonic acid | 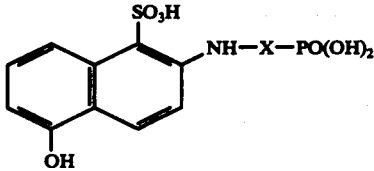 | (32) |
| | and 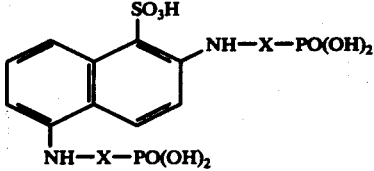 | (33) |
| 2,5-diaminonaphthalene-1-sulphonic acid<br>2,8-dihydroxynaphthalene-6-sulphonic acid<br><br>2-amino-8-naphthol-6-sulphonic acid<br><br>2-methylamino-8-naphthol-6-sulphonic acid<br><br>1-amino-8-naphthol-5-sulphonic acid | Formula (33)<br>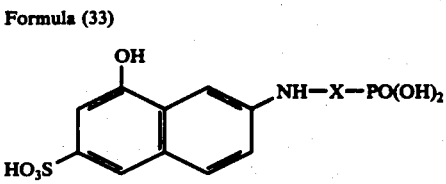 | (34) |
| | 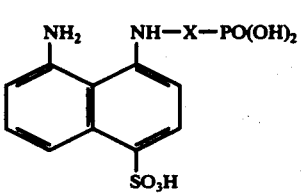 | (35) |

As examples of compounds of formula (3) which can be used, there may be mentioned:

1-aminomethylphosphonic acid
2-aminoethylphosphonic acid
3-aminopropylphosphonic
4-aminobutylphosphonic acid
5-aminopentylphosphonic acid
6-aminohexylphosphonic acid
-amino-1-methylethylphosphonic acid
2-amino-1-methylethylphosphonic acid
1-amino-3-methylbutylphosphonic acid
2-amino-1-hydroxypropylphosphonic acid
3-amino-2-hydroxypropylphosphonic acid
α-aminobenzylphosphonic acid
α-aminophenylethylphosphonic acid
3- or 4-aminobenzylphosphonic acid
2, 3- or 4-aminophenylphosphonic acid
3-amino-4-methylphenylphosphonic acid
4-amino-2-fluorophenylphosphonic acid
2-amino-5-chlorophenylphosphonic acid
3-amino-4-chlorophenylphosphonic acid
4-amino-2-bromophenylphosphonic acid
4-amino-3-nitrophenylphosphonic acid
4-n-butylamino-3-nitrophenylphosphonic acid
1-naphthylamine-6-phosphonc acid
1-naphthylamine-7-phosphonic acid
7-phosphono-2-naphthylamine-5-sulphonic acid
2-naphthylamine-7-phosphonic acid
8-sulpho-2-naphthylamine-3-phosphonic acid
6,8-disulpho-1-naphthylamino-3-phosphonic acid.

As alkali-metal bisulphite, there may be used potassium bisulphite, but it is preferred to use sodium bisulphite. As a general rule, the amount of alkali metal bisulphite used is greater than 1 mole per mole of naphthalene compound.

The naphthalene compounds of formula (1) in which $n$ is 0 and $p$ is 1, can alternatively be obtained by heating together a compound of the formula:

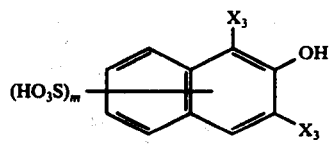
(36)

or

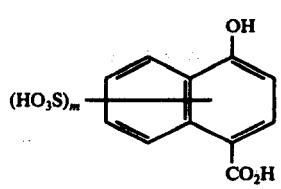
(37)

in which $m$ has the meaning stated above preferably 0 or 1, and one $X_3$ is H and the other is $CO_2H$, and an amine of formula (3) wherein X has the meaning stated above, in the presence of an aqueous solution of an alkali metal bisulphite.

This alternative process can be carried out in a similar manner to the process described above, with the proviso that it is usually possible to effect the reaction at slightly lower temperatures, e.g. from 80° C upwards, than is the case when using compounds of formula (2) as a reactant. The preferred range of reaction temperature is 80°–150° C.

As examples of compounds of formulae (36) and (37), there may be mentioned:

2-hydroxy-1 and 3-naphthoic acids
1-hydroxy-4-naphthoic acid
6- and 8-sulpho-2-hydroxy-3-naphthoic acids
4- and 7-sulpho-2-hydroxy-1-naphthoic acids.

The new naphthalene compounds can be used as dyestuff intermediates, e.g. in most cases as coupling components for the manufacture of azo dyes by coupling with aromatic diazonium salts in similar manner to other N-substituted naphthylamines.

The new compounds having a 1-amino-4-anilino- or 1,4-dianilinonaphthalene structure, the benzene ring containing a phosphonic acid group, are useful as intermediates for the synthesis of sulphur dyes. Those having a 2,6- or 2,7-dianilinonaphthalene structure are useful for the synthesis of azine dyes.

The invention is illustrated by the following Examples in which parts and percentages are by weight:

EXAMPLE 1

A mixture of sodium bisuphite liquor (40%) (97 parts), sodium hydroxide liquor (S.G. 1.35, 35.6 parts) and sodium chloride (5.75 parts) is stirred and heated to 80° C. 2,8-dihydroxynaphthalene-6-sulphonic acid (44.9 parts) and m-aminophenylphosphonic acid (34,6 parts) are then charged and the mixture is stirred and boiled under reflux for 17 hours, then cooled to 60° C. 43.6 parts of 36% aqueous hydrochloric acid are added to give an acid reaction on Congo Red paper. During the acidification the temperature is raised steadily to boiling point and the viscous reaction mass diluted progressively with water (40 parts). The mobile suspension is then boiled under reflux for 1½–2 hours until evolution of sulphur dioxide has essentially ceased. During this period samples are spotted on to Congo Red test paper to confirm a positive acid reaction. The suspension is then cooled to 10°–20° C and stirred for a further 2 hours.

It is then filtered and the cake is washed with 10 parts of cold water. The paste (150 parts) is dried in air at 50°–60° C to give 99.5 parts at 74% strength of 2-(3-phosphonophenylamino-8-naphthol-6-sulphonic acid.

Infra-red spectrum: The product showed strong peaks at 1595, 1180 and 655 cm$^{-1}$, medium strength peaks at 3550, 3380, 1535, 1105, 1060, 790 and 695 cm$^{-1}$ and weak peaks at 1280 and 930 cm$^{-1}$.

Further examples of the invention, which are listed in column III of the Table below, may be obtained by the method described in Example 1. The parts of 3-aminophenylphosphonic acid used in that Example are replaced by an equivalent amount of the amine listed in column II of the Table.

| Example | Amine | New naphthalene compound |
| --- | --- | --- |
| 2 | 2-aminoethylphosphonic acid | 1-hydroxy-7-(2-phosphonoethylamino)-3-sulphonaphthalene |
| 3 | 3-aminopropylphosphonic acid | 1-hydroxy-7-(3-phosphonopropylamino)-3- |

-continued

| Example | Amine | New naphthalene compound |
|---|---|---|
| 4 | 4-aminobenzylphosphonic acid | sulphonaphthalene 1-hydroxy-7-(4-phosphonomethylphenylamino)-3-sulphonaphthalene |
| 5 | 4-aminophenylphosphonic acid | 1-hydroxy-7-(4-phosphonophenylamino)-3-sulphonaphthalene |
| 6 | 3-amino-4-methylphenylphosphonic acid | 1-hydroxy-7-(2-methyl-5-phosphonophenylamino)-3-sulphonaphthalene |
| 7 | 3-amino-4-methoxyphenylphosphonic acid | 1-hydroxy-7-(2-methoxy-5-phosphonophenylamino)-3-sulphonaphthalene |

EXAMPLE 8

Sodium bisulphite liquor (40% — 23 parts), sodium hydroxide liquor (70° Tw — 8.1 parts), salt (1.8 parts), 1-amino-6-sulphonaphtalene (11.2 parts) and 3-aminophenylphosphonic acid (10.4 parts) are heated in a sealed tube for 10 hours at 130° C. After cooling the tube is opened and hydrochloric acid (36% - 13.9 parts) is added until an acid reaction is obtained on Congo Red paper. The suspension is boiled under reflux for 1 hour until evolution of sulphur dioxide has essentially ceased. During this period samples are spotted on to Congo Red paper to confirm acid reaction. The suspension is cooled to room temperature and filtered. The filtrate is set stirring and sodium chloride (8 parts = 20% wt/vol) added. After stirring for 18 hours the suspension is filtered under vacuum and the cake pressed well to remove mothers liquor. The paste (8 parts) is dried in air at 50°-60° C to give 7 parts of 1-(3-phosphonophenylamino)-6-sulphonaphthalene.

EXAMPLE 9

Sodium bisulphite liquor (40% — 260 parts), water (100 parts), 2-hydroxy-6-sulphonaphthalene (56 parts) and 3-aminophenylphosphonic acid (49.8 parts) are set stirring and heated at 40° C. Sodium hydroxide liquor (70° Tw — 97.2 parts) is added and the mixture boiled under reflux for 18 hours. After cooling to 80° C the suspension is acidified with hydrochloric acid (36% — 177 parts) until acid reaction is obtained on Congo Red paper. During acidification the temperature is raised steadily to the boiling point and the suspension is boiled under reflux for 1-2 hours until evolution of sulphur dioxide has essentially ceased. During this period samples are spotted onto Congo Red test paper to confirm a positive acid reaction. The suspension is then cooled to 10°-20° C and stirred for a further 2 hours. It is then filtered and the filter cake suspended in water (approximately 500 parts). The suspension is heated and the solution obtained on boiling gently is allowed to cool to 10°-20° C. The suspension formed is filtered and the paste is dried in vacuum at 40° C to give 123 parts at 50.7% strength of 2-(3-phosphenophenylamino)-6-sulphonaphthalene.

Infra-red spectrum: The product showed a strong peak at 1190 cm$^{-1}$, moderate strength peaks at 1595, 1240, 1115, 725 and 690 cm$^{-1}$ and weak peaks at 3420, 950, 870 and 790 cm$^{-1}$.

EXAMPLE 10

Sodium bisulphite liquor (40% — 24.2 parts), sodium hydroxide liquor (70° Tw — 8.9 parts) and salt (1.5 parts) are set stirring. 6-amino-1-hydroxy-3-sulphonaphthalene (11.2 parts) and 3-aminophenyl phosphonic acid (8.7 parts) are then charged and the mixture is boiled under reflux for 18 hours. After cooling to 80° C the mass is acidified with hydrochloric acid (36% — 17.7 parts) until acid reaction is obtained on Congo Red paper. The suspension is boiled under reflux for 1-2 hours until evolution of sulphur dioxide has essentially ceased. During this period samples are spotted onto Congo Red test paper to confirm a positive acid reaction. The suspension is then cooled to room temperature and filtered and the cake washed with (10 parts). The filtrate and wash are combined as 1-hydroxy-6-(3-phosphonophenylamino)-3-sulphonaphthalene liquor.

EXAMPLE 11

Water (20 parts) is set stirring and 2-hydroxy-3-naphthoic acid (9.5 parts) charged. Sodium hydroxide liquor (70° Tw — 6.8 parts) is then added until an alkaline reaction is obtained on Brilliant Yellow test paper. 3-aminophenylphosphonic acid (8.7 parts) and sodium bisulphite liquor (40% — 100 parts) are charged and the mixture is stirred and boiled under reflux for 18 hours. Carbon dioxide is evolved during the early part of the boiling period. After cooling to 80° C the suspension is acidified with hydrochloric acid (36% — 59 parts) until acid reaction is obtained on Congo Red paper. During acidification the temperature is raised steadily to the boiling point and the suspension is boiled under reflux for 1-2 hours until evolution of sulphur dioxide has essentially ceased. During this period samples are spotted on to Congo Red test paper to confirm a positive acid reaction. The suspension is then cooled to room temperature, filtered and the cake washed with water (10 parts). The paste (18.2 parts) is dried an air at 50° C to give 12.9 parts of 2-(3-phosphonophenylamino)-naphthalene.

Infra-red spectrum: The product showed strong peaks at 1595, 1160, 940 and 690 cm$^{-1}$, moderate strength peaks at 3410, 1525, 1245, 820 and 745 cm$^{-1}$ and a weak peak at 1315 cm$^{-1}$.

We claim:
1. A naphthalene compound of the formula

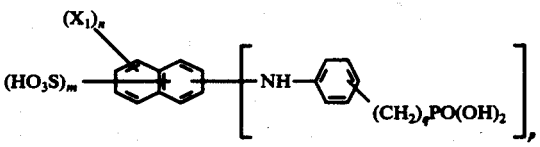

wherein
  $m$ is 0, 1 or 2
  $n$ is 0 or can be 1 if $m$ is 1 or 2 in which case $X_1$ is OH or $NH_2$ in $m$ position to a $SO_3H$ group,
  $p$ is 1 or 2,
  $q$ is 0 or 1 and
  the benzene ring can be further substituted by $OCH_3$ or $CH_3$.

2. A naphthalene compound of the formula

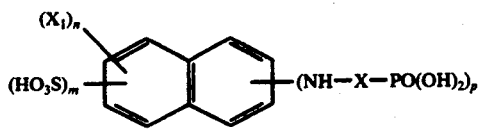
wherein
m is 0, 1 or 2,
n is 0 or can be 1 if m is 1 or 2, in which case $X_1$ is NH$_2$ or OH in m position to a SO$_3$H group,
X is phenylene, tolylene or anisylene, and p is 1 or 2.
3. The naphthalene compound of claim 2 having the formula
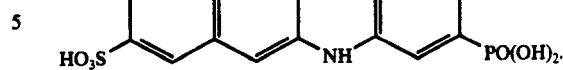
4. The naphthalene compound of claim 2 having the formula
5. The naphthalene compound of claim 2 having the formula
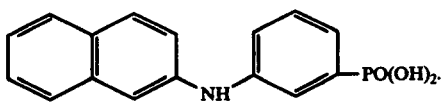
* * * * *